United States Patent [19]

Streicher et al.

[11] Patent Number: 5,763,641
[45] Date of Patent: Jun. 9, 1998

[54] PROCESS FOR THE PREPARATION OF AROMATIC METHOXYCARBOXYLIC ACID METHYL ESTERS

[75] Inventors: Willi Streicher, Krefeld; Hans-Joachim Laakmann, Leichlingen, both of Germany

[73] Assignee: Bayer Aktiengesellschaft, Leverkusen, Germany

[21] Appl. No.: 785,375

[22] Filed: Jan. 17, 1997

[30] Foreign Application Priority Data

Jan. 31, 1996 [DE] Germany ............... 196 03 329.2

[51] Int. Cl.$^6$ .................................................. C07C 69/76
[52] U.S. Cl. .................................................. 560/64; 560/56
[58] Field of Search ........................... 560/64, 56

[56] References Cited

U.S. PATENT DOCUMENTS

| | | | |
|---|---|---|---|
| 4,501,920 | 2/1985 | Periasamy | 560/64 |
| 4,739,100 | 4/1988 | Adrian et al. | |
| 4,808,748 | 2/1989 | Lin et al. | |
| 5,424,479 | 6/1995 | Müller et al. | |

FOREIGN PATENT DOCUMENTS

| | | |
|---|---|---|
| 0059596 | 9/1982 | European Pat. Off. |
| 0083228 | 7/1983 | European Pat. Off. |
| 0200840 | 11/1986 | European Pat. Off. |
| 0208840 | 1/1987 | European Pat. Off. |
| 0307519 | 3/1989 | European Pat. Off. |
| 0640582 | 3/1995 | European Pat. Off. |

OTHER PUBLICATIONS

F. Dallacker, et al., Darstellung von Derivaten des Trimethoxybenzols, Monatshefte for Chemie, Bd. 91, pp. 1077–1088, (1960).

A. Werner, et al., Zur Kenntniss einer neuen Esterificirungsmethode für organische Säuren, Ber. Dt. Chem. Ges., 37, pp. 3658–3661, (1904).

H. Wieland, Die Oxydation des p–Anisidins und Dimethyl–p–anisidins, Ber. Dt. Chem. Ges., 43, pp. 712–728, (1910).

*Primary Examiner*—Paul J. Killos
*Attorney, Agent, or Firm*—Sprung Kramer Schaefer & Briscoe

[57] ABSTRACT

In a process, improved in respect of yield, purity and simple procedure, for the preparation of aromatic methoxycarboxylic acid methyl esters by methylation of the corresponding aromatic hydroxycarboxylic acids with dimethyl sulfate in the presence of water and a base, a procedure is followed in which the water, base and aromatic hydroxycarboxylic acid are initially introduced into the reaction vessel, 1 to 2.5 times the molar amount of dimethyl sulfate (based on the methylatable hydroxyl and carboxyl groups) is metered in and, during this procedure, the pH of the reaction mixture is controlled by addition of an aqueous base in finely divided form.

10 Claims, No Drawings

PROCESS FOR THE PREPARATION OF AROMATIC METHOXYCARBOXYLIC ACID METHYL ESTERS

The present invention relates to a particularly advantageous process for the preparation of aromatic methoxycarboxylic acid methyl esters by methylation of aromatic hydroxycarboxylic acids with dimethyl sulfate.

Aromatic methoxycarboxylic acid methyl esters are valuable synthesis units, for example for the preparation of active compounds and polyesters. Thus, for example, methyl 6-methoxy-1-naphthoate is important as an intermediate product for the preparation of agents for prevention and treatment of late symptoms of diabetes mellitus (cf. EP Laid-Open Specifications 59 596, 200 840 and 307 519 and U.S. Pat. No. 4,808,748) and methyl 3-methoxy-4-methylbenzoate is important as an intermediate product for the preparation of agents for treatment of asthma and bronchitis (cf. EP Laid-Open Specification 83 228).

It is known in principle that aromatic hydroxycarboxylic acids can be alkylated with dialkyl sulfates (cf., for example, Organikum, 15th edition, pages 252–255 and Houben-Weyl, 4th edition, Volume 6/3, pages 62–66). A disadvantage here is that to achieve virtually complete conversions and high contents of products alkylated both on the hydroxyl function and on the carboxyl function, large excesses of dialkyl sulfates have to be employed (cf., for example, Monatshefte für Chemie 91, 1077 (1960) —6.4 times the molar amount of dimethyl sulfate and 75% yield —, EP-PS 208 840 —3.4 times the molar amount of dimethyl sulfate and 77% yield of an only 87% pure product —and Ber. Dt. Chem. Ges. 37, 3658 (1904) —2 times the molar amount and 70% yield).

Smaller amounts of dialkyl sulfates can also be employed, but other disadvantages then have to be accepted. Thus, the procedure described in Ber. Dt. Chem. Ges. 40, 714 (1910), in which the total amount of reactants and auxiliaries is first brought together and then heated to the reaction temperature, is not suitable for a procedure on an industrial scale, since the heat of reaction suddenly released by this method leads to an uncontrollable and non-reproducible progress of the reaction.

The process of EP Laid-Open Specification 640 582 does not start from aromatic hydroxycarboxylic acids as such, but from mixtures of aromatic hydroxycarboxylic acids with aromatic methoxycarboxylic acids. When this process is carried out in practice, a procedure is followed in which the aromatic hydroxycarboxylic acid is first reacted with dimethyl sulfate, the desired product (=aromatic methoxycarboxylic acid methyl ester) is first separated off from the reaction mixture, followed by an only partly methylated product (=aromatic methoxycarboxylic acid), and the aromatic methoxycarboxylic acid separated off is added to the next batch. In addition to the expenditure needed for separating off and recycling the particular aromatic methoxycarboxylic acid, the space/time yield of this process is unfavorable. Although according to Example 1 of EP Laid-Open Specification 640 582 the yield of aromatic hydroxycarboxylic acid methyl ester is 96%, based on the fresh aromatic hydroxycarboxylic acid employed, it is only 63.7% based on the two starting materials from which aromatic methoxycarboxylic acid methyl esters can be formed (aromatic hydroxycarboxylic acid and aromatic methoxycarboxylic acid). The reaction mixture then contains 36% of monoalkylated aromatic hydroxycarboxylic acid (=aromatic methoxycarboxylic acid). The circumstances are similar in the other examples of EP Laid-Open Specification 640 582.

There is thus still a need for a process for the preparation of aromatic methoxycarboylic acid methyl esters in which, at the same time, little dimethyl sulfate can be employed, working is easy and the target product can be obtained in high yields and purities.

A process has now been found for the preparation of aromatic methoxycarboxylic acid methyl esters by methylation of the corresponding aromatic hydroxycarboxlic acids with dimethyl sulfate in the presence of water and a base, which comprises initially introducing the water, base and aromatic hydroxycarboxylic acid into the reaction vessel, metering in 1 to 2.5 times the molar amount of dimethyl sulfate (based on methylatable hydroxyl and carboxyl groups), and controlling the pH of the reaction mixture during this procedure by addition of aqueous base in finely divided form.

Aromatic hydroxycarboxylic acids which can be employed in the process according to the invention are, for example, those of the formula (I)

HO-Ar-COOH    (I), in which

Ar represents an optionally substituted phenyl or naphthyl radical, and aromatic methoxycarboxylic acid methyl esters of the formula (II)

CH₃O-Ar-COOCH₃    (II), in which

Ar has the meaning given in the case of formula (I), can thus be prepared.

If Ar in the formulae (I) and (II) are phenyl radicals, these can optionally contain, for example, 1 or 2 identical or different substituents. If Ar in the formulae (I) and (II) are naphthyl radicals, these can optionally contain, for example, 1, 2 or 3 identical or different substituents. Possible substituents for Ar are, for example, halogen atoms, in particular fluorine, chlorine and bromine, alkyl groups, in particular those having 1 to 4 C atoms, alkylene groups, in particular those having 2 to 5 C atoms, alkoxy groups, in particular those having 1 to 4 C atoms, benzyloxy groups, halogenoalkyl groups, in particular those having 1 to 3 fluorine, chlorine and/or bromine atoms and 1 to 4 C atoms, nitro groups, cyano groups and/or alkoxycarbonyl groups, in particular those having 1 to 4 C atoms in the alkoxy part. The substituents can be in various positions on the radical Ar, and, in the case of polynuclear radicals Ar, they can be arranged in various positions on one or more nuclei.

Examples of alkyl groups are methyl, ethyl, n-propyl, i-propyl, n-butyl, s-butyl and t-butyl. Examples of alkylene groups are vinyl, allyl, methallyl, 2-butenyl and 1,1-dimethylallyl. Examples of alkoxy groups are methoxy, ethoxy, n-propoxy, i-propoxy, n-butoxy, s-butoxy and t-butoxy. Examples of halogenoalkyl groups are chloromethyl, dichloromethyl, trichloromethyl, fluoromethyl, difluoromethyl, trifluoromethyl, chlorodifluoromethyl, dichlorofluoromethyl, 2,2,2-trichloroethyl, 2,2,2-trifluoroethyl, 1,1-dichloroethyl, 1,1-difluoroethyl, perfluoroethyl and perchloroethyl. Examples of alkoxycarbonyl groups are methoxycarbonyl, ethoxycarbonyl, i-propoxycarbonyl, n-propoxycarbonyl, n-butoxycarbonyl, s-butoxycarbonyl and t-butoxycarbonyl.

Preferably, aromatic hydroxycarboxylic acids of the formula (III)

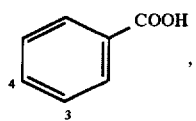

which contain an OH group in the 3- or 4-position and optionally 1 or 2 $C_1$–$C_4$-alkyl groups, in particular methyl groups, on otherwise unoccupied positions, and of the formula (IV)

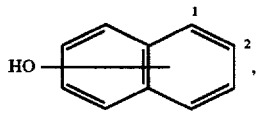

which contain a COOH group in the 1- or 2-position and optionally 1 or 2 $C_1$–$C_4$-alkyl groups, in particular methyl groups, on otherwise free positions, are employed in the process according to the invention, and the corresponding aromatic methoxycarboxylic acid methyl esters are prepared.

3-Hydroxy-4-methylbenzoic acid or 6-hydroxy-1-naphthoic acid is especially preferably employed and methyl 3-methoxy-4-methylbenzoate or methyl 6-methoxy-1-naphthoate prepared.

The aromatic hydroxycarboxylic acids to be employed in the process according to the invention are known compounds or can be prepared analogously to known aromatic hydroxycarboxylic acids.

75 to 200 g of water, for example, per mol of aromatic hydroxycarboxylic acid employed can be employed in the process according to the invention. This amount is preferably 100 to 180 g. According to the invention, the water is added in two ways. On the one hand, some of the water is initially introduced together with the base and aromatic hydroxycarboxylic acid, and on the other hand an aqueous base is added to the reaction mixture in finely divided form to control the pH of the reaction mixture. A procedure is preferably followed in which at least an amount of water such that the reaction mixture is stirrable is initially introduced, and at least an amount of water is added to the base for controlling the pH such that this base can be added to the reaction mixture as an aqueous solution.

Possible bases for the process according to the invention are any desired bases, in particular water-soluble bases, which are capable of splitting off the phenolic and the carboxylic acid hydrogen atoms from the particular aromatic hydroxycarboxylic acid of the formula (I) and which cause no troublesome side reactions under the reaction conditions. In particular, these are bases which are not methylated by dimethyl sulfate. Inorganic bases, in particular alkali metal hydroxides, such as sodium and potassium hydroxide, are preferred. The bases are preferably employed in the form of an aqueous solution. Such aqueous solutions can have any desired concentration, for example between 10 and 50% by weight.

The base is preferably added in total in at least an amount which is sufficient to deprotonate all the OH and COOH groups introduced with the aromatic hydroxycarboxylic acid employed. That is to say, preferably at least two equivalents of base are employed per mole of aromatic hydroxycarboxylic acid. The upper amount of base can be, for example, up to 3 equivalents per mole of aromatic hydroxycarboxylic acid employed. The use of 2.01 to 2.5 equivalents of base per mol of aromatic hydroxycarboxylic acid employed is preferred.

The base is added in the process according to the invention in two ways. One portion, for example at least one equivalent (based on the aromatic hydroxycarboxylic acid), is preferably initially introduced together with the aromatic hydroxycarboxylic acid and water. The remainder of the base is added to the reaction mixture as an aqueous solution in finely divided form during metering in of the dimethyl sulfate, and thus the pH of the reaction mixture is controlled.

It is advantageous to control the pH of the reaction mixture such that the addition of, for example, 60 to 90% by weight, preferably 70 to 85% by weight, of the total dimethyl sulfate employed takes place at a higher pH and the addition of the remaining dimethyl sulfate takes place at a lower pH. What pH values are optimum for which hydroxycarboxylic acid can be determined by routine series of experiments if necessary. In general, good results are obtained if the first portion of dimethyl sulfate is added at a pH, for example, in the range of from 10 to 13, preferably 10.5 to 12.5, and the remaining portion of the dimethyl sulfate is added, for example, at a pH, for example, in the range from 7 to 10, preferably 7.5 to 9.5. It is furthermore advantageous to allow the pH to vary within the stated ranges, for example, by not more than one, preferably not more than 0.8, units.

According to the invention, the pH is controlled during the addition of dimethyl sulfate by addition of an aqueous base in finely divided form. This aqueous base can be, for example, a 20 to 50% strength by weight, preferably 40 to 50% strength by weight, aqueous solution of a base. The same base formulation which is also used for initially introducing the water, base and aromatic hydroxycarboxlic acid together is expediently used for controlling the pH during the addition of dimethyl sulfate.

Dimethyl sulfate is preferably employed in an amount of 1.2 to 2.1 mol per mol of aromatic hydroxycarboxylic acid.

Fine division of the aqueous base during control of the pH exists, for example, if the aqueous base is added in the form of droplets, the diameter of which is less than 1000 μm. This diameter is preferably less than 800 μm, in particular less than 500 μm. Such droplets can be obtained if the aqueous base is metered in, for example, through a nozzle. The most diverse nozzles can be used for this. Examples which may be mentioned are full cone, fan jet and two-component nozzles.

The reaction temperature in the process according to the invention can be, for example, in the range from 10° to 90° C. It is preferably between 15° and 80° C., in particular 20° to 70° C. It is often advantageous to start the process according to the invention at a relatively low temperature, for example at 10° to 40° C., preferably 15° to 35° C., and to bring it to completion at a higher temperature, for example at 30° to 90° C., preferably at 40° to 80° C.

The process according to the invention is in general carried out under normal pressure. It can also be carried out under increased or reduced pressure.

The procedure described thus far for the process according to the invention corresponds to a discontinuous embodiment. However, the process according to the invention can also be carried out continuously, for example by carrying it out in a flow-through reactor into which the dimethyl sulfate and aqueous base (the latter in finely divided form) are metered in one or more zones, the pH being controlled.

It is advantageous to ensure thorough mixing of the reaction mixture while carrying out the process according to the invention.

The reaction mixture present after the process according to the invention has been carried out can be worked up in a manner known per se, for example by filtration, centrifugation, phase separation, extraction, distillation (including vacuum and/or steam distillation) and/or in accordance with the principle of pH separation. Sufficiently pure aromatic methoxycarboxylic acid methyl esters are often already obtained when the stirrer is switched off after the end of the reaction and the two phases are allowed to separate. The upper (organic) phase then often comprises the aromatic methoxycarboxylic acid methyl ester prepared in yields of more than 90% of theory, based on the methylatable compounds employed, and in purities of more than 98%.

The process according to the invention has a number of advantages. In the process, the dimethyl sulfate employed is utilized better than in other processes. Partly methylated products, for example aromatic methoxycarboxylic acids, are formed only in traces, if at all. Specific removal and recycling thereof is therefore not necessary. Aromatic methoxycarboxylic acid methyl esters are obtained in high yields and purities. The process according to the invention can be carried out in a simple manner and allows high space/time yields. Overall, it is thus considerably more favorable than the known processes for the preparation of aromatic methoxycarboxylic acid methyl esters.

EXAMPLES

Example 1

1,490 l of water were initially introduced into an 8 m³ reactor at room temperature. 1,198 kg of 3-hydroxy-4-methylbenzoic acid were then introduced, and a pH of 11.5 was subsequently established with 50% strength aqueous sodium hydroxide solution. 1,780 kg of dimethyl sulfate were then allowed to run in, while cooling at 20° C., in the course of 4 hours, and the pH was kept between 11.2 and 11.8 by addition of 50% strength by weight aqueous sodium hydroxide solution via a two-component nozzle in the form of droplets of diameter 200 µm. Thereafter, the reaction mixture was heated to 55° C. and a further 500 kg of dimethyl sulfate were metered in at this temperature in the course of 4 hours, the pH being controlled as before, but this time in a range from 8.2 to 9.0. When the reaction had ended, the batch was left to stand undisturbed, two phases forming. The lower aqueous phase was separated off. The upper organic phase comprised 1,362 kg of methyl 3-methoxy-4-methylbenzoate. This corresponds to a yield of 95% of theory, based on the methylatable compounds employed. The methyl 3-methoxy-4-methylbenzoate thus obtained had a purity of more than 98% (GC).

Example 2

3,100 l of water were initially introduced into an 8 m³ reactor at room temperature. 1,450.4 kg of p-hydroxybenzoic acid were then introduced, a pH of 11.5 was then established with 50% strength by weight aqueous sodium hydroxide solution, and finally 1,560 kg of dimethyl sulfate were allowed to run in, while cooling at 18° to 25° C., in the course of 4 hours. During this procedure, the pH was kept between 11.2 and 11.8 with very finely divided sodium hydroxide solution metered in via a two-component atomizing nozzle. The reaction mixture was then heated to 55° C. A further 1,350.6 kg of dimethyl sulfate were metered in at this temperature in the course of 4 hours and the pH was kept between 8.2 and 9.0 in the manner described above. When the reaction had ended, the two phases were allowed to separate. The upper organic phase comprised 1,743 kg of methyl p-methoxybenzoate. This corresponds to a yield of 96% of theory, based on the methylatable compounds employed. The methyl p-methoxybenzoate thus obtained contained a hydroxybenzoic acid and less than 0.1% of paranisic acid (=4-methoxybenzoic acid).

Example 3

1.5 l of water were initially introduced into a 5 l three-necked flask at room temperature, and 461 g of 6-hydroxy-2-naphthoic acid were then introduced. A pH of 11.5 was then established with 50% strength by weight aqueous sodium hydroxide solution and 710 g of dimethyl sulfate were subsequently allowed to run in, while cooling at 18° to 25° C., in the course of 6 hours, the pH being kept between 11.2 and 11.8 by metering in very finely divided sodium hydroxide solution via a two-component atomizing nozzle. When the reaction had ended, the solid product was filtered off with suction. 899.2 g of methyl 6-methoxy-2-naphthoate were thus obtained. This corresponds to a yield of 97.2%, based on the methylatable compounds employed. The methyl 6-methoxy-2-naphthoate thus obtained had a purity of more than 57% (HPLC) and contained less than 0.1% by weight of 6-hydroxy-2-naphthoic acid.

What is claimed is:

1. In a process for the preparation of an aromatic methoxycarboxylic acid methyl ester by methylation of the corresponding aromatic hydroxycarboxylic acid with dimethyl sulfate in the presence of water and a base, wherein the water, base and aromatic hydroxycarboxylic acid are initially introduced into the reaction vessel, and 1 to 2.5 times the molar amount of dimethyl sulfate (based on the methylatable hydroxyl and carboxyl groups) is metered in, the improvement which comprises controlling the pH of the reaction mixture by adding an aqueous base in finely divided form.

2. The process as claimed in claim 1, wherein an aromatic hydroxycarboxylic acid of the formula

HO—Ar—COOH          (I), in which

Ar represents an optionally substituted phenyl or naphthyl radical, is employed and an aromatic methoxycarboxylic acid methyl ester of the formula (II)

CH₃O—Ar—COOCH₃          (II), in which

Ar has the meaning given in the case of formula (I), is prepared.

3. The process as claimed in claim 2, wherein Ar are phenyl radicals which are unsubstituted or substituted by 1 or 2 identical or different substituents, or naphthyl radicals which are unsubstituted or substituted by 1, 2 or 3 identical or different substituents, the substituents being chosen from the group consisting of halogen atoms, alkyl groups having 1 to 4 C atoms, alkylene groups having 2 to 5 C atoms, alkoxy groups having 1 to 4 C atoms, the benzyloxy group, halogenoalkyl groups having 1 to 3 fluorine, chlorine and/or bromine atoms and 1 to 4 C atoms, the nitro group, the cyano group and alkoxycarbonyl groups having 1 to 4 C atoms in the alkoxy part.

4. The process as claimed in claim 1, wherein 75 to 200 g of water are employed per mol of aromatic hydroxycarboxylic acid employed.

5. The process as claimed in claim 1, wherein at least an amount of water such that the reaction mixture is stirrable is initially introduced, and at least an amount of water is added to the base for controlling the pH such that this base can be added to the reaction mixture as an aqueous solution.

6. The process as claimed in claim 1, wherein a total of 2 to 3 equivalents of base are employed per mol of aromatic hydroxycarboxylic acid.

7. The process as claimed in claim 1, herein at least one equivalent of the base is initially introduced together with the aromatic hydroxycarboxylic acid and water.

8. The process as claimed in claim 1, wherein 60 to 90% by weight of the dimethyl sulfate employed is added at a pH in the range from 10 to 13 and the remaining dimethyl sulfate is added at a pH of 7 to 10.

9. The process as claimed in claim 1, wherein the aqueous base is added in the form of droplets, the diameter of which is less than 1000 µm.

10. The process as claimed in claim 1, which is carried out at temperatures in the range from 10° to 90° C.

* * * * *

UNITED STATES PATENT AND TRADEMARK OFFICE
CERTIFICATE OF CORRECTION

PATENT NO. : 5,763,641
DATED : June 9, 1998
INVENTOR(S) : Streicher, et al.

It is certified that error appears in the above-indentified patent and that said Letters Patent is hereby corrected as shown below:

Col. 7, claim 7 line 1   Delete " herein " and substitute -- wherein --

Signed and Sealed this

Twentieth Day of October, 1998

Attest:

BRUCE LEHMAN

*Attesting Officer*   *Commissioner of Patents and Trademarks*